(12) United States Patent
Johns et al.

(10) Patent No.: US 8,217,034 B2
(45) Date of Patent: Jul. 10, 2012

(54) CHEMICAL COMPOUNDS

(75) Inventors: Brian Alvin Johns, Research Triangle Park, NC (US); Jason Gordon Weatherhead, Research Triangle Park, NC (US); Toshikazu Hakogi, Osaka (JP); Yasunori Aoyama, Osaka (JP)

(73) Assignees: Shionogi & Co., Ltd., Osaka (JP); GlaxoSmithKline LLC, Philadelphia, PA (US)

( * ) Notice: Subject to any disclaimer, the term of this patent is extended or adjusted under 35 U.S.C. 154(b) by 0 days.

(21) Appl. No.: 13/054,633

(22) PCT Filed: Jul. 23, 2009

(86) PCT No.: PCT/US2009/051497
§ 371 (c)(1),
(2), (4) Date: Apr. 8, 2011

(87) PCT Pub. No.: WO2010/011812
PCT Pub. Date: Jan. 28, 2010

(65) Prior Publication Data
US 2011/0190236 A1    Aug. 4, 2011

Related U.S. Application Data

(60) Provisional application No. 61/083,612, filed on Jul. 25, 2008.

(51) Int. Cl.
*A61K 31/535*    (2006.01)
*C07D 498/14*    (2006.01)
(52) U.S. Cl. ...................... 514/230.2; 544/95
(58) Field of Classification Search ............ 544/95; 514/230.2
See application file for complete search history.

(56) References Cited

U.S. PATENT DOCUMENTS

| 2006/0116356 A1 | 6/2006 | Cai et al. |
| 2007/0072831 A1 | 3/2007 | Cai et al. |
| 2008/0161271 A1 | 7/2008 | Yoshida et al. |

FOREIGN PATENT DOCUMENTS

WO    2006/116764    11/2006

OTHER PUBLICATIONS

Cecil Textbook of Medicine (20th Edition, vol. 2, 1996, pp. 1739-1747).*
International Search Report issued Oct. 2, 2009 in International (PCT) Application No. PCT/US2009/051497 along with the Written Opinion.
Supplementary European Search Report issued Sep. 28, 2011 in Application No. 09800989.7.
J. D. Thomas, "Improving the Topical Delivery of Phenol-Containing Drugs: An Alkylcarbonyloxymethyl and Alkyloxycarbonyloxymethyl Prodrug Approach", University of Florida, pp. 1-136, Dec. 31, 2006.
J. D. Thomas et al., "Overcoming Steric Effects in the Coupling Reaction of Alkyloxycarbonyloxymethyl (AOCOM) Halides with Phenols: An Efficient Synthesis of AOCOM Phenolic Prodrugs", Tetrahedron Letters, vol. 48, No. 1, pp. 109-112, Nov. 30, 2007.

* cited by examiner

*Primary Examiner* — Kahsay T Habte
(74) *Attorney, Agent, or Firm* — Wenderoth, Lind & Ponack, L.L.P.

(57) ABSTRACT

The present invention features compounds that are prodrugs of HIIV integrase inhibitors and therefore are useful in the inhibition of HIV replication, the prevention and/or treatment of infection by HIV, and in the treatment of AIDS and/or ARC.

10 Claims, 1 Drawing Sheet

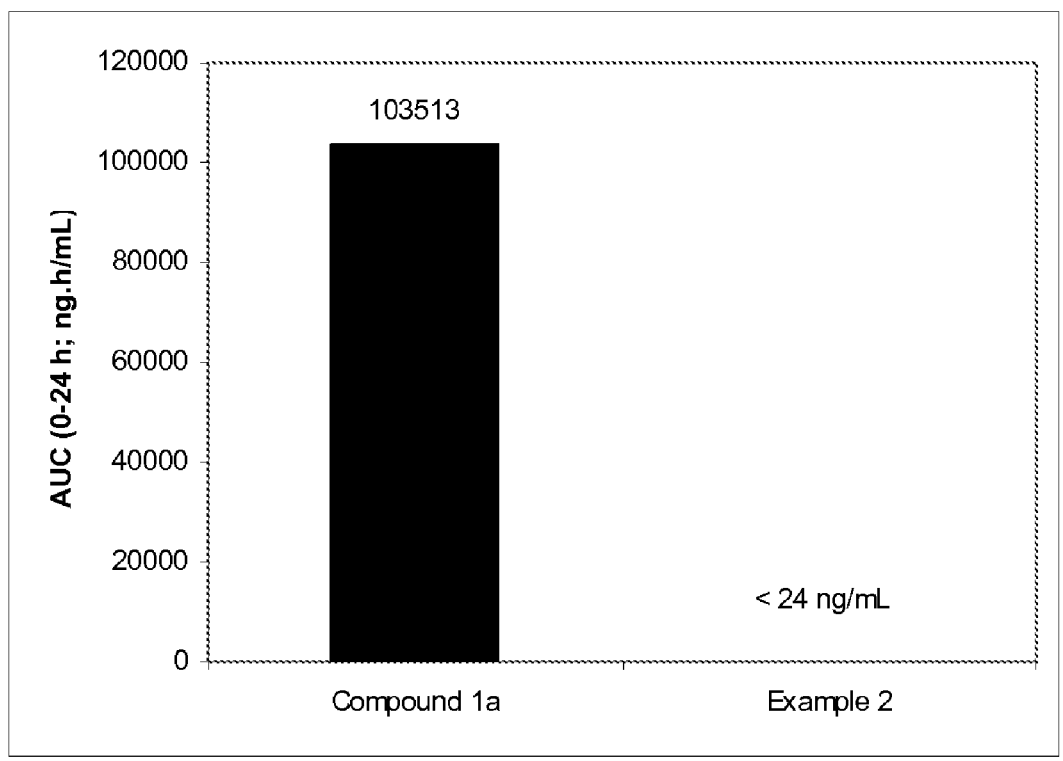

CHEMICAL COMPOUNDS

This application is a U.S. national stage of International Application No. PCT/US2009/051497 filed Jul. 23, 2009, which claims the benefit of U.S. application Ser. No. 61/083,612 filed Jul. 25, 2008.

BACKGROUND OF THE INVENTION

The human immunodeficiency virus ("HIV") is the causative agent for acquired immunodeficiency syndrome ("AIDS"), a disease characterized by the destruction of the immune system, particularly of $CD4^+$ T-cells, with attendant susceptibility to opportunistic infections, and its precursor AIDS-related complex ("ARC"), a syndrome characterized by symptoms such as persistent generalized lymphadenopathy, fever and weight loss. HIV is a retrovirus; the conversion of its RNA to DNA is accomplished through the action of the enzyme reverse transcriptase. Compounds that inhibit the function of reverse transcriptase inhibit replication of HIV in infected cells. Such compounds are useful in the prevention or treatment of HIV infection in humans.

A required step in HIV replication in human T-cells is the insertion by virally-encoded integrase of proviral DNA into the host cell genome. Integration is believed to be mediated by integrase in a process involving assembly of a stable nucleoprotein complex with viral DNA sequences, cleavage of two nucleotides from the 3' termini of the linear proviral DNA and covalent joining of the recessed 3' OH termini of the proviral DNA at a staggered cut made at the host target site. The repair synthesis of the resultant gap may be accomplished by cellular enzymes.

There is continued need to find new therapeutic agents to treat human diseases. HIV integrase is an attractive target for the discovery of new therapeutics due to its important role in viral infections, particularly HIV infections. Integrase inhibitors are disclosed in WO2006/116724. Integrase inhibitors are disclosed in WO2006/116724. The compounds of the present invention were designed to deliver active therapeutic agents.

SUMMARY OF THE INVENTION

The present invention features compounds that are prodrugs of HIV integrase inhibitors and therefore are useful in the inhibition of HIV replication, the prevention and/or treatment of infection by HIV, and in the treatment of AIDS and/or ARC. The present invention features compounds of formula (I):

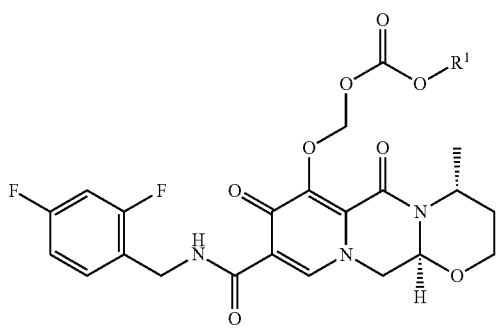

wherein:
$R^1$ is $C_1$-$C_8$alkyl or $LR^2$;
L is alkylene;
$R^2$ is
a) hydroxy;
b) alkoxy;
c) $OR^3$ wherein $R^3$ is $P(O)(OH)_2$ or alkoxy;
d) heterocyclyl optionally substituted with oxo or $C_1$-$C_8$alkyl;
e) $C(O)OR^4$ wherein $R^4$ is H, $C_1$-$C_8$alkyl, or $XR^5$ wherein X is alkylene and $R^5$ is $C_8$-$C_{10}$aryl, heterocyclyl, or $NR^6R^7$ wherein $R^6$ and $R^7$ are independently selected from the group consisting of H and $C_1$-$C_8$alkyl;
f) $NR^6R^7$;
g) $C(O)NR^8R^9$ wherein $R^8$ and $R^9$ are independently selected from the group consisting of H and $XR^5$; or
h) $C(O)R^{10}$ wherein $R^{10}$ is heterocyclyl optionally substituted with $XR^{11}$ wherein $R^{11}$ is heterocyclyl;
or a pharmaceutically acceptable salt thereof.

BRIEF DESCRIPTION OF THE DRAWINGS

FIG. 1: Plasma concentrations of: (4R,12aS)-N-[(2,4-Difluorophenyl)methyl]-7-hydroxy-4-methyl-6,8-dioxo-3,4,6,8,12,12a-hexahydro-2H-pyrido[1',2':4,5]pyrazino[2,1-b][1,3]oxazine-9-carboxamide (compound 1a of Scheme 2) and a prodrug, Example 2.

DETAILED DESCRIPTION OF THE INVENTION

The present invention features compounds of formula (I):

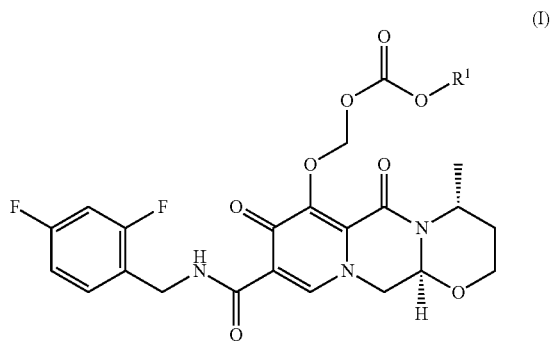

wherein:
$R^1$ is $C_1$-$C_8$alkyl or $LR^2$;
L is alkylene;
$R^2$ is
a) hydroxy;
b) alkoxy;
c) $OR^3$ wherein $R^3$ is $P(O)(OH)_2$ or alkoxy;
d) heterocyclyl optionally substituted with oxo or $C_1$-$C_8$alkyl;
e) $C(O)OR^4$ wherein $R^4$ is H, $C_1$-$C_8$alkyl, or $XR^5$ wherein X is alkylene and $R^5$ is $C_8$-$C_{10}$aryl, heterocyclyl, or $NR^6R^7$ wherein $R^6$ and $R^7$ are independently selected from the group consisting of H and $C_1$-$C_8$alkyl;
f) $NR^6R^7$;
g) $C(O)NR^8R^9$ wherein $R^8$ and $R^9$ are independently selected from the group consisting of H and $XR^5$; or
h) $C(O)R^{10}$ wherein $R^{10}$ is heterocyclyl optionally substituted with $XR^{11}$ wherein $R^{11}$ is heterocyclyl;
or a pharmaceutically acceptable salt thereof.

The present invention also features compounds of formula (I) wherein $R^1$ is $C_{1-8}$alkyl or a pharmaceutically acceptable salt thereof.

The present invention also features compounds of formula (I) wherein $R^1$ is $LR^2$ wherein L is $C_{1-8}$alkylene and $R^2$ is hydroxy, or a pharmaceutically acceptable salt thereof.

The present invention also features compounds of formula (I) wherein $R^1$ is $LR^2$ wherein L is $C_{1-8}$alkylene and $R^2$ and —OP(O)(OH)$_2$ or a pharmaceutically acceptable salt thereof.

The present invention also features compounds of formula (I) wherein $R^1$ is $LR^2$ wherein L is $C_{1-8}$alkylene and $R^2$ and heterocyclyl or a pharmaceutically acceptable salt thereof.

The present invention also features compounds of formula (I) selected from the group consisting of:

{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl methyl carbonate;

{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(methyloxy)ethyl carbonate;

{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-hydroxyethyl carbonate;

{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(phosphonooxy)ethyl carbonate;

{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(4-morpholinyl)ethyl carbonate; and pharmaceutically acceptable salts thereof.

The term "alkyl", alone or in combination with any other term, refers to a straight-chain or branched-chain saturated aliphatic hydrocarbon radical containing the specified number of carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkylene" refers to a straight or branched chain divalent hydrocarbon radical, preferably having from one to twelve carbon atoms, unless otherwise defined. Examples of "alkylene" as used herein include, but are not limited to, methylene, ethylene, propylene, butylene, isobutylene and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl" alone or in combination with any other term, refers to a carbocyclic aromatic moiety (such as phenyl or naphthyl) containing the specified number of carbon atoms, preferably from 6-10 carbon atoms. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like. Unless otherwise indicated, the term "aryl" also includes each possible positional isomer of an aromatic hydrocarbon radical, such as in 1-naphthyl, 2-naphthyl, 5-tetrahydronaphthyl, 6-tetrahydronaphthyl, 1-phenanthridinyl, 2-phenanthridinyl, 3-phenanthridinyl, 4-phenanthridinyl, 7-phenanthridinyl, 8-phenanthridinyl, 9-phenanthridinyl and 10-phenanthridinyl. Examples of aryl radicals include, but are not limited to, phenyl, naphthyl, indenyl, azulenyl, fluorenyl, anthracenyl, phenanthrenyl, tetrahydronaphthyl, indanyl, phenanthridinyl and the like.

The term "heterocycle," "heterocyclic," and "heterocyclyl" as used herein, refer to a 3- to 7-membered monocyclic heterocyclic ring or 8- to 11-membered bicyclic heterocyclic ring system any ring of which is either saturated, partially saturated or unsaturated, and which may be optionally benzofused if monocyclic. Each heterocycle consists of one or more carbon atoms and from one to four heteroatoms selected from the group consisting of N, O and S, and wherein the nitrogen and sulfur heteroatoms may optionally be oxidized, and the nitrogen atom may optionally be quaternized, and including any bicyclic group in which any of the above-defined heterocyclic rings is fused to a benzene ring. The heterocyclic ring may be attached at any carbon or heteroatom, provided that the attachment results in the creation of a stable structure. Preferred heterocycles include 5-7 membered monocyclic heterocycles and 8-10 membered bicyclic heterocycles. When the heterocyclic ring has substituents, it is understood that the substituents may be attached to any atom in the ring, whether a heteroatom or a carbon atom, provided that a stable chemical structure results. "Heteroaromatics" or "heteroaryl" are included within the heterocycles as defined above and generally refers to a heterocycle in which the ring system is an aromatic monocyclic or polycyclic ring radical containing five to twenty carbon atoms, preferably five to ten carbon atoms, in which one or more ring carbons, preferably one to four, are each replaced by a heteroatom such as N, O, S and P. Preferred heteroaryl groups include 5-6 membered monocyclic heteroaryls and 8-10 membered bicyclic heteroaryls. Also included within the scope of the term "heterocycle, "heterocyclic" or "heterocyclyl" is a group in which a non-aromatic heteroatom-containing ring is fused to one or more aromatic rings, such as in an indolinyl, chromanyl, phenanthridinyl or tetrahydro-quinolinyl, where the radical or point of attachment is on the non-aromatic heteroatom-containing ring. Unless otherwise indicated, the term "heterocycle, "heterocyclic" or "heterocyclyl" also included each possible positional isomer of a heterocyclic radical, such as in 1-indolinyl, 2-indolinyl, 3-indolinyl. Examples of heterocycles include imidazolyl, imidazolinoyl, imidazolidinyl, quinolyl, isoquinolyl, indolyl, indazolyl, indazolinolyl, perhydropyridazyl, pyridazyl, pyridyl, pyrrolyl, pyrrolinyl, pyrrolidinyl, pyrazolyl, pyrazinyl, quinoxolyl, piperidinyl, pyranyl, pyrazolinyl, piperazinyl, pyrimidinyl, pyridazinyl, morpholinyl, thiamorpholinyl, furyl, thienyl, triazolyl, thiazolyl, carbolinyl, tetrazolyl, thiazolidinyl, benzofuranoyl, thiamorpholinyl sulfone, oxazolyl, oxadiazolyl, benzoxazolyl, oxopiperidinyl, oxopyrrolidinyl, oxoazepinyl, azepinyl, isoxozolyl, isothiazolyl, furazanyl, tetrahydropyranyl, tetrahydrofuranyl, thiazolyl, thiadiazoyl, dioxolyl, dioxinyl, oxathiolyl, benzodioxolyl, dithiolyl, thiophenyl, tetrahydrothiophenyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term "heteroatom" means nitrogen, oxygen, or sulfur and includes any oxidized form of nitrogen, such as N(O) {$N^+$—$O^-$} and sulfur such as S(O) and S(O)$_2$, and the quaternized form of any basic nitrogen.

A combination of substituents or variables is permissible only if such a combination results in a stable or chemically feasible compound Unless otherwise stated, structures depicted herein are also meant to include all stereochemical forms of the structure, i.e., the R and S configurations for each asymmetric center. Therefore, racemates and racemic mixtures, single enantiomers, diastereomeric mixtures and individual diastereoisomers of the present compounds are expressly included within the scope of the invention. Although the specific compounds exemplified herein may be depicted in a particular stereochemical configuration, compounds having either the opposite stereochemistry at any given chiral center or mixtures thereof are also envisioned.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by a $^{13}C$- or $^{14}C$-enriched carbon are also within the scope of this invention.

It will be apparent to one skilled in the art that certain compounds of this invention may exist in alternative tautomeric forms. All such tautomeric forms of the present compounds are within the scope of the invention. Unless otherwise indicated, the representation of either tautomer is meant to include the other.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. The term "prophylactically effective amount" refers to an amount effective in preventing a virus infection, for example an HIV infection, or preventing the occurrence of symptoms of such an infection, in a patient. As used herein, the term "patient" refers to a mammal, including a human.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the antiviral agent.

The term "treatment" as used herein refers to the alleviation of symptoms of a particular disorder in a patient, or the improvement of an ascertainable measurement associated with a particular disorder, and may include the suppression of symptom recurrence in an asymptomatic patient such as a patient in whom a viral infection has become latent. Treatment includes prophylaxis which refers to preventing a disease or condition or preventing the occurrence of symptoms of such a disease or condition, in a patient. As used herein, the term "patient" refers to a mammal, including a human.

As used herein, the term "subject" refers to a patient, animal or a biological sample. The term "biological sample", as used herein, includes, without limitation, cell cultures or extracts thereof; preparations of an enzyme suitable for in vitro assay; biopsied material obtained from a mammal or extracts thereof; and blood, saliva, urine, feces, semen, tears, or other body fluids or extracts thereof.

Pharmaceutically acceptable salts of the compounds according to the invention include those derived from pharmaceutically acceptable inorganic and organic acids and bases. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric, methanesulfonic, ethanesulfonic, formic, benzoic, malonic, naphthalene-2-sulfonic and benzenesulfonic acids. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g. sodium), alkaline earth metal (e.g., magnesium), ammonium, $NW_4^+$ (wherein W is $C_{1-4}$ alkyl) and other amine salts. Physiologically acceptable salts of a hydrogen atom or an amino group include salts or organic carboxylic acids such as acetic, lactic, tartaric, malic, isethionic, lactobionic and succinic acids; organic sulfonic acids such as methanesulfonic, ethanesulfonic, benzenesulfonic and p-toluenesulfonic acids and inorganic acids such as hydrochloric, sulfuric, phosphoric and sulfamic acids. Physiologically acceptable salts of a compound with a hydroxy group include the anion of said compound in combination with a suitable cation such as $Na^+$, $NH_4^+$, and $NW_4^+$ (wherein W is a $C_{1-4}$alkyl group). Preferred salts include sodium, calcium, potassium and hydrochloride.

Other compounds of this invention may be prepared by one skilled in the art following the teachings of the specification coupled with knowledge in the art using reagents that are readily synthesized or commercially available.

Any reference to any of the above compounds also includes a reference to a pharmaceutically acceptable salt thereof.

Salts of the compounds of the present invention may be made by methods known to a person skilled in the art. For example, treatment of a compound of the present invention with an appropriate base or acid in an appropriate solvent will yield the corresponding salt.

Compounds of the present invention are useful as prodrugs to deliver therapeutic compounds, for examples compounds disclosed in WO2006/116764, which were demonstrated to have HIV integrase inhibitory activity. One aspect of the instant invention relates to methods of treating or preventing viral infection, for example an HIV infection, in a biological sample comprising contacting the biological sample with compounds of formula (I) or pharmaceutically acceptable salts thereof. Another aspect of the instant invention relates to methods of treating or preventing viral infection, for example, an HIV infection, in a patient comprising administering to the patient a therapeutically effective amount of compounds of formula (I) or (Ia) or pharmaceutically acceptable salts thereof.

The compounds according to the invention are particularly suited to the treatment or prophylaxis of HIV infections and associated conditions. Reference herein to treatment extends to prophylaxis as well as the treatment of established infections, symptoms, and associated clinical conditions such as AIDS related complex (ARC), Kaposi's sarcoma, and AIDS dementia.

According to one embodiment of the invention, compounds of formula (I) or salts thereof may be formulated into compositions. In a preferred embodiment, the composition is a pharmaceutical composition, which comprises a compound of formula (I) and pharmaceutically acceptable carrier, adjuvant or vehicle. In one embodiment, the composition comprises an amount of a compound of the present invention effective to treat or prevent viral infection, for example an HIV infection, in a biological sample or in a patient. In another embodiment, compounds of this invention and pharmaceutical compositions thereof, which comprise an amount of a compound of the present innovation effective to inhibit viral replication or to treat or prevent a viral infection or disease or disorder, for example an HIV infection, and a pharmaceutically acceptable carrier, adjuvant or vehicle, may be formulated for administration to a patient, for example, for oral administration.

The present invention features compounds according to the invention for use in medical therapy, for example for the treatment or prophylaxis of a viral infection, for example an HIV infection and associated conditions. The compounds according to the invention are especially useful for the treatment of AIDS and related clinical conditions such as AIDS related complex (ARC), progressive generalized lymphadenopathy (PGL), Kaposi's sarcoma, thrombocytopenic purpura, AIDS-related neurological conditions such as AIDS dementia complex, multiple sclerosis or tropical paraperesis, anti-HIV antibody-positive and HIV-positive conditions, including such conditions in asymptomatic patients.

According to another aspect, the present invention provides a method for the treatment or prevention of the symptoms or effects of a viral infection in an infected patient, for example, a mammal including a human, which comprises administering to said patient a pharmaceutically effective amount of a compound according to the invention. According to one aspect of the invention, the viral infection is a retroviral infection, in particular an HIV infection.

The present invention further includes the use of a compound according to the invention in the manufacture of a medicament for administration to a subject for the treatment of a viral infection, in particular and HIV infection.

The compounds according to the invention may also be used in adjuvant therapy in the treatment of HIV infections or HIV-associated symptoms or effects, for example Kaposi's sarcoma.

The present invention further provides a method for the treatment of a clinical condition in a patient, for example, a mammal including a human which clinical condition includes those which have been discussed hereinbefore, which comprises treating said patient with a pharmaceutically effective amount of a compound according to the invention. The present invention also includes a method for the treatment or prophylaxis of any of the aforementioned diseases or conditions.

Reference herein to treatment extends to prophylaxis as well as the treatment of established conditions, disorders and infections, symptoms thereof, and associated. The above compounds according to the invention and their pharmaceutically acceptable salts may be employed in combination with other therapeutic agents for the treatment of the above infections or conditions. Combination therapies according to the present invention comprise the administration of a compound of the present invention or a pharmaceutically acceptable salt thereof and another pharmaceutically active agent. The active ingredient(s) and pharmaceutically active agents may be administered simultaneously (i.e., concurrently) in either the same or different pharmaceutical compositions or sequentially in any order. The amounts of the active ingredient(s) and pharmaceutically active agent(s) and the relative timings of administration will be selected in order to achieve the desired combined therapeutic effect.

Examples of other therapeutic agents include:
Nucleotide reverse transcriptase inhibitors such as zidovudine, didanosine, lamivudine, zalcitabine, abacavir, stavidine, adefovir, adefovir dipivoxil, fozivudine, todoxil, emtricitabine, alovudine, amdoxovir, elvucitabine, and similar agents;
Non-nucleotide reverse transcriptase inhibitors (including an agent having anti-oxidation activity such as immunocal, oltipraz, etc.) such as nevirapine, delavirdine, efavirenz, loviride, immunocal, oltipraz, capravirine, TMC-278, TMC-125, etravirine, and similar agents;
Protease inhibitors such as saquinavir, ritonavir, indinavir, nelfinavir, amprenavir, fosamprenavir, brecanavir, raltegravir, atazanavir, tipranavir, palinavir, lasinavir, and similar agents;
Entry inhibitors such as enfuvirtide (T-20), T-1249, PRO-542, PRO-140, TNX-355, BMS-806, 5-Helix and similar agents;
Integrase inhibitors such as L-870,810, raltegravir and similar agents;
Budding inhibitors such as PA-344 and PA-457, and similar agents; and
CXCR4 and/or CCR5 inhibitors such as vicriviroc (Sch-C), Sch-D, TAK779, maraviroc (UK 427,857), TAK449 and similar agents.

The present invention further includes the use of a compound according to the invention in the manufacture of a medicament for simultaneous or sequential administration with at least another therapeutic agent, such as those defined hereinbefore.

Compounds of the present invention may be administered with an agent known to inhibit or reduce the metabolism of compounds, for example ritonavir. Accordingly, the present invention features a method for the treatment or prophylaxis of a disease as hereinbefore described by administration of a compound of the present invention in combination with a metabolic inhibitor. Such combination may be administered simultaneously or sequentially.

In general a suitable dose for each of the above-mentioned conditions will be in the range of 0.01 to 250 mg per kilogram body weight of the recipient (e.g. a human) per day, preferably in the range of 0.01 to 100 mg per kilogram body weight per day. Unless otherwise indicated, all weights of active ingredient are calculated as the parent compound of formula (I); for salts or esters thereof, the weights would be increased proportionally. The desired dose may be presented as one, two, three, four, five, six or more sub-doses administered at appropriate intervals throughout the day. In some cases the desired dose may be given on alternative days. These sub-doses may be administered in unit dosage forms, for example, containing 1 to 1000 mg, 20 to 500 mg, 10 to 500 mg, or 1 to 400 mg of active ingredient per unit dosage form.

While it is possible for the active ingredient to be administered alone, it is preferable to present it as a pharmaceutical composition. The compositions of the present invention comprise at least one active ingredient, as defined above, together with one or more acceptable carriers thereof and optionally other therapeutic agents. Each carrier must be acceptable in the sense of being compatible with the other ingredients of the composition and not injurious to the patient.

Pharmaceutical compositions include those suitable for oral, rectal, nasal, topical (including transdermal, buccal and sublingual), vaginal or parenteral (including subcutaneous, intramuscular, intravenous, intradermal, and intravitreal) administration. The compositions may conveniently be presented in unit dosage form and may be prepared by any methods well known in the art of pharmacy. Such methods represent a further feature of the present invention and include the step of bringing into association the active ingredients with the carrier, which constitutes one or more accessory ingredients. In general, the compositions are prepared by uniformly and intimately bringing into association the active ingredients with liquid carriers or finely divided solid carriers or both, and then if necessary shaping the product.

The present invention further includes a pharmaceutical composition as hereinbefore defined wherein a compound of the present invention or a pharmaceutically acceptable salt thereof and another therapeutic agent are presented separately from one another as a kit of parts.

Compositions suitable for transdermal administration may be presented as discrete patches adapted to remain in intimate contact with the epidermis of the recipient for a prolonged period of time. Such patches suitably contain the active compound 1) in an optionally buffered, aqueous solution or 2) dissolved and/or dispersed in an adhesive or 3) dispersed in a polymer. A suitable concentration of the active compound is about 1% to 25%, preferably about 3% to 15%. As one particular possibility, the active compound may be delivered from the patch by electrotransport or iontophoresis as generally described in *Pharmaceutical Research* 3(6), 318 (1986).

Pharmaceutical compositions of the present invention suitable for oral administration may be presented as discrete units such as capsules, caplets, cachets or tablets each containing a predetermined amount of the active ingredients; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredients in a free-flowing form such as a powder or granules, optionally mixed with a binder (e.g. povidone, gelatin, hydroxypropylmethyl cellulose), lubricant, inert diluent, preservative, disintegrant (e.g. sodium starch glycollate, cross-linked povidone, cross-linked sodium carboxymethyl cellulose) surface-active or dispersing agent. Molded tablets may be made by molding a mixture of the powdered compound moistened with an inert liquid diluent in a suitable machine. The tablets may optionally be coated or scored and may be formulated so as to provide slow or controlled release of the active ingredients therein using, for example, hydroxypropylmethyl cellulose in varying proportions to provide the desired release profile. Tablets may optionally be provided with an enteric coating, to provide release in parts of the gut other than the stomach.

Pharmaceutical compositions suitable for topical administration in the mouth include lozenges comprising the active ingredients in a flavored base, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions suitable for vaginal administration may be presented as pessaries, tampons, creams, gels, pastes, foams or spray. Pharmaceutical compositions may contain in addition to the active ingredient such carriers as are known in the art to be appropriate.

Pharmaceutical compositions for rectal administration may be presented as a suppository with a suitable carrier comprising, for example, cocoa butter or a salicylate or other materials commonly used in the art. The suppositories may be conveniently formed by admixture of the active combination with the softened or melted carrier(s) followed by chilling and shaping in molds.

Pharmaceutical compositions suitable for parenteral administration include aqueous and nonaqueous isotonic sterile injection solutions which may contain anti-oxidants, buffers, bacteriostats and solutes which render the pharmaceutical composition isotonic with the blood of the intended recipient; and aqueous and non-aqueous sterile suspensions which may include suspending agents and thickening agents; and liposomes or other microparticulate systems which are designed to target the compound to blood components or one or more organs. The pharmaceutical compositions may be presented in unit-dose or multi-dose sealed containers, for example, ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

Unit dosage pharmaceutical compositions include those containing a daily dose or daily subdose of the active ingredients, as hereinbefore recited, or an appropriate fraction thereof.

It should be understood that in addition to the ingredients particularly mentioned above the pharmaceutical compositions of this invention may include other agents conventional in the art having regard to the type of pharmaceutical composition in question, for example, those suitable for oral administration may include such further agents as sweeteners, thickeners and flavoring agents.

The compounds of the present invention may be prepared according to the following reactions schemes and examples, or modifications thereof using readily available starting materials, reagents and conventional synthesis procedures. In these reactions, it is also possible to make use of variants which are known to those of ordinary skill in the art.

(4R,12aS)-N-[(2,4-Difluorophenyl)methyl]-7-hydroxy-4-methyl-6,8-dioxo-3,4,6,8,12,12a-hexahydro-2H-pyrido[1′,2′:4,5]pyrazino[2,1-b][1,3]oxazine-9-carboxamide can be prepared by methods known to those skilled in the art, including methods disclosed in WO2006/116724.

Scheme 1

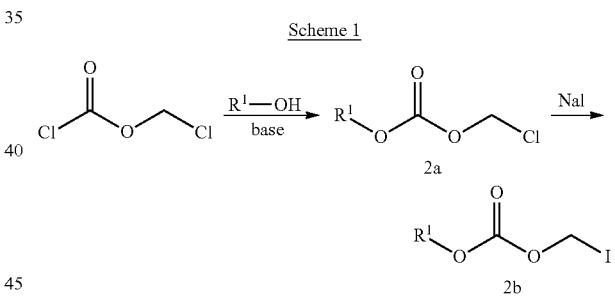

Scheme 2

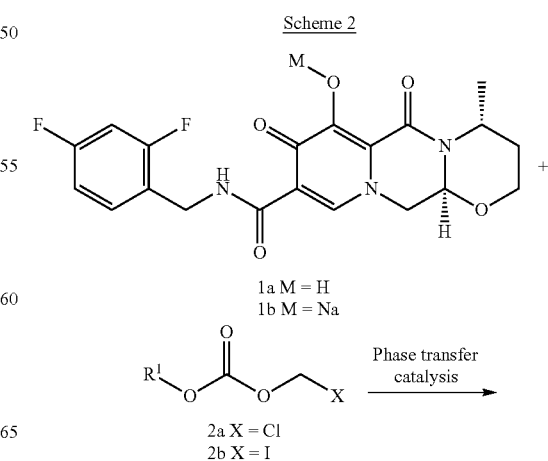

1a M = H
1b M = Na

2a X = Cl
2b X = I

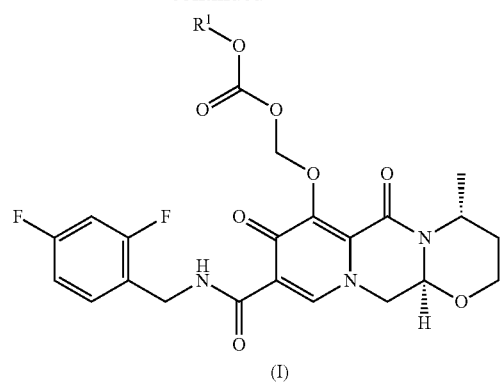
(I)
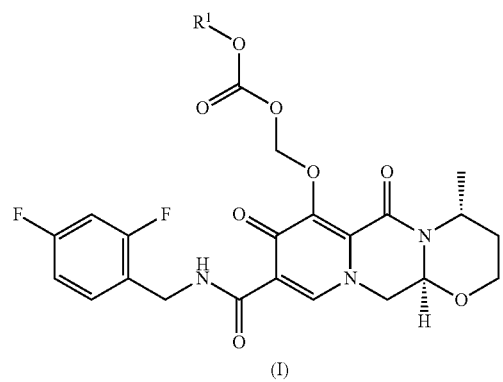
(I)
Scheme 3
Z = H, Me
(Ia)
Scheme 4
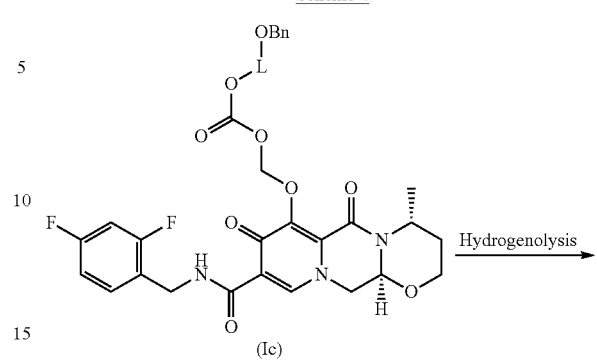
(Ic)
Hydrogenolysis
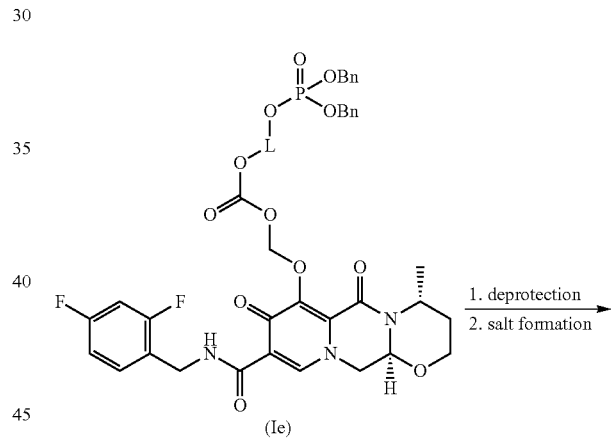
(Id)
phosphorylation
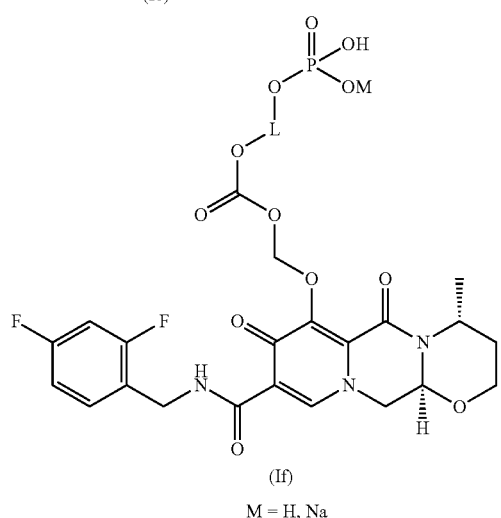
(Ie)
1. deprotection
2. salt formation
(If)
M = H, Na Scheme 5
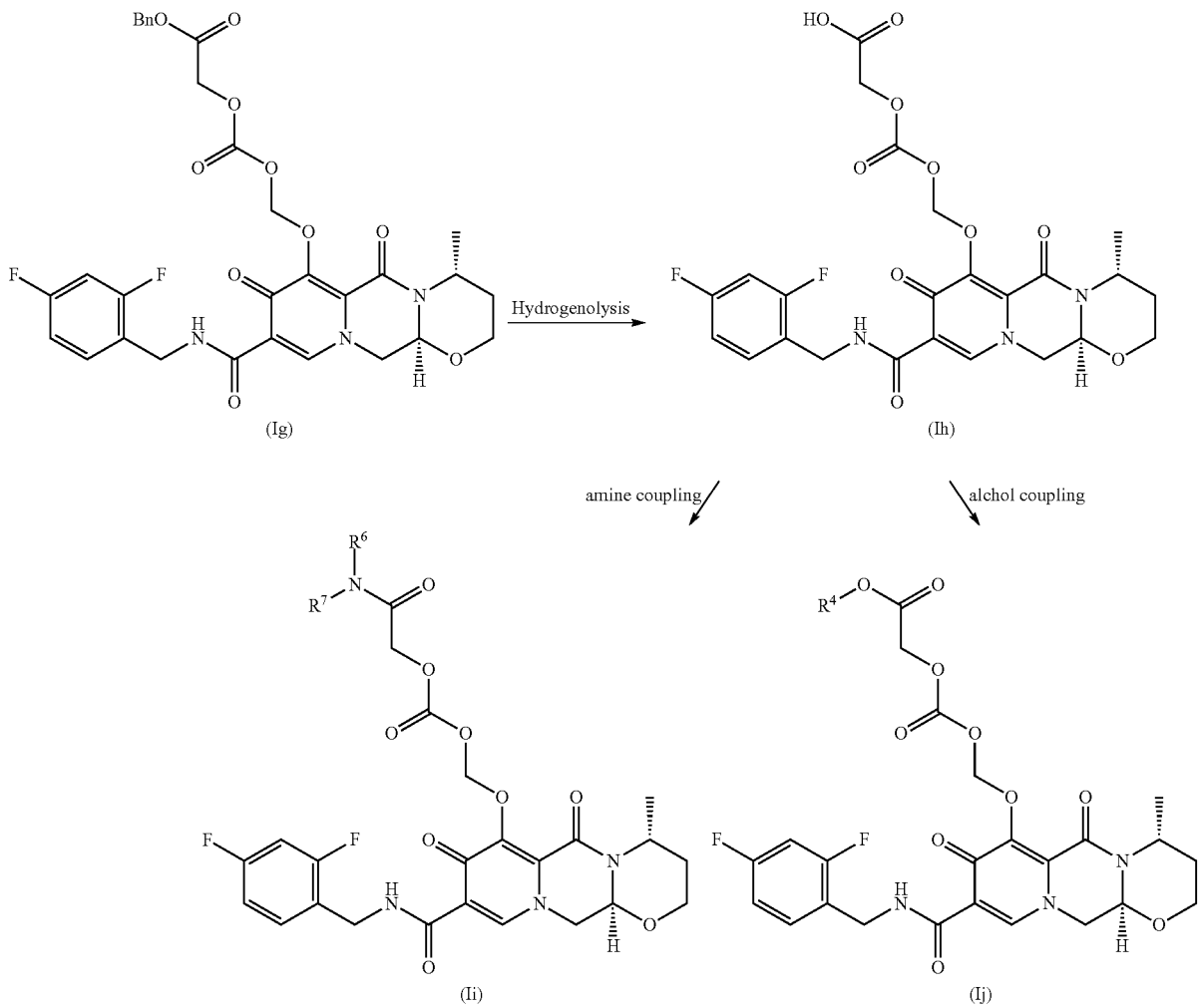
The following examples are intended for illustration only and are not intended to limit the scope of the invention in any way.
Preparation 1
(4R,12aS)-N-[(2,4-Difluorophenyl)methyl]-7-hydroxy-4-methyl-6,8-dioxo-3,4,6,8,12,12a-hexahydro-2H-pyrido[1',2':4,5]pyrazino[2,1-b][1,3]oxazine-9-carboxamide sodium salt (compound 1b, scheme 2)
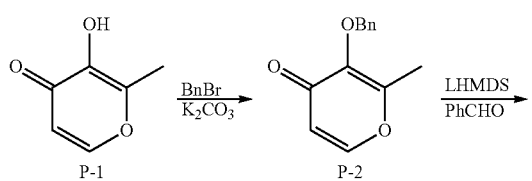
-continued
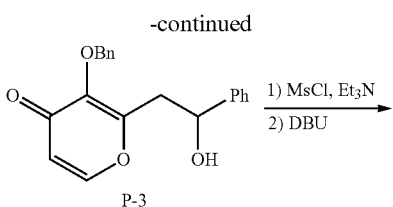
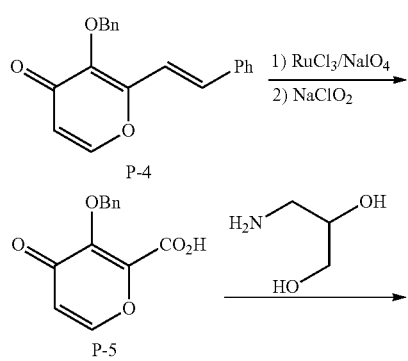

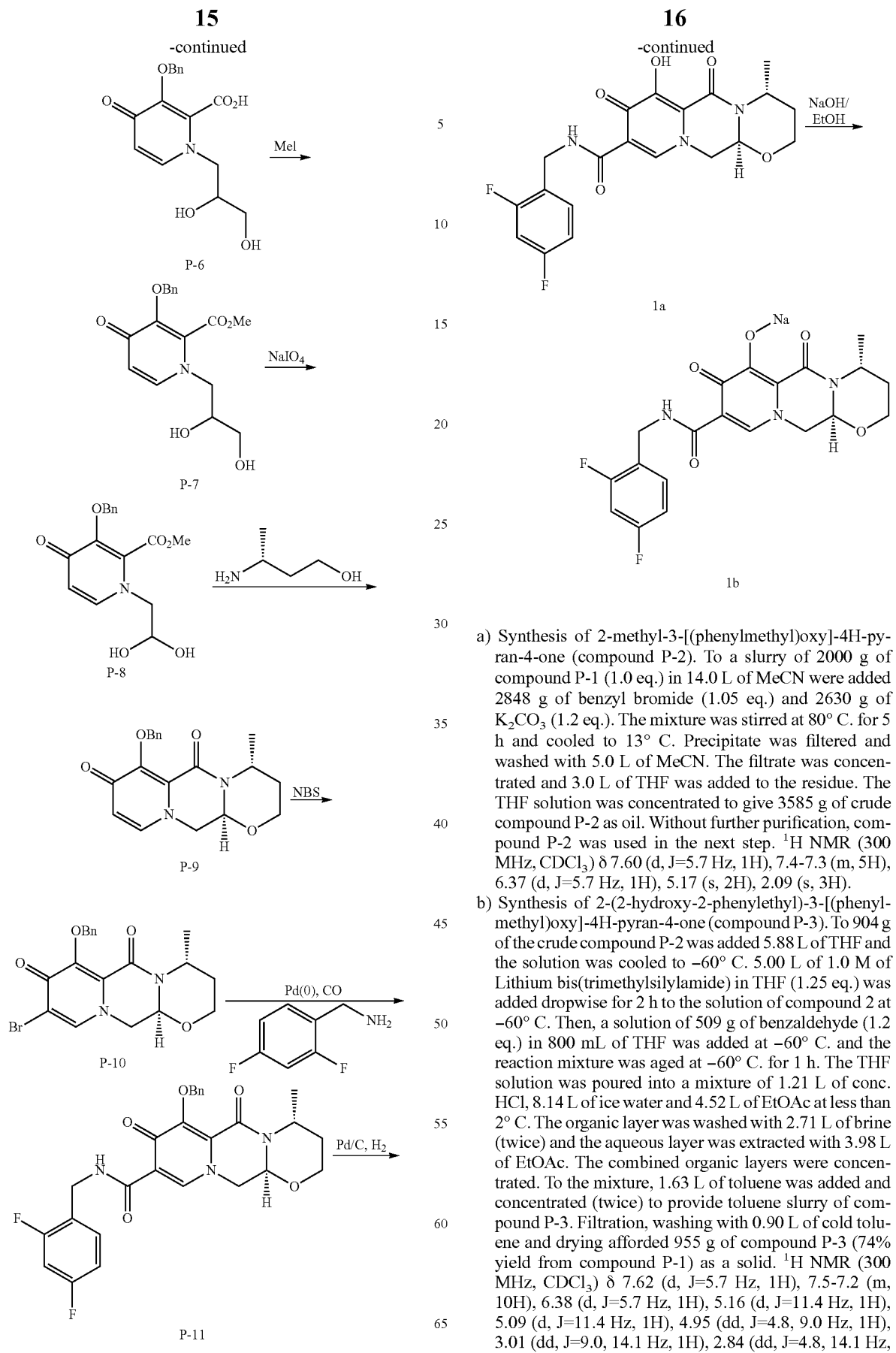

a) Synthesis of 2-methyl-3-[(phenylmethyl)oxy]-4H-pyran-4-one (compound P-2). To a slurry of 2000 g of compound P-1 (1.0 eq.) in 14.0 L of MeCN were added 2848 g of benzyl bromide (1.05 eq.) and 2630 g of $K_2CO_3$ (1.2 eq.). The mixture was stirred at 80° C. for 5 h and cooled to 13° C. Precipitate was filtered and washed with 5.0 L of MeCN. The filtrate was concentrated and 3.0 L of THF was added to the residue. The THF solution was concentrated to give 3585 g of crude compound P-2 as oil. Without further purification, compound P-2 was used in the next step. $^1$H NMR (300 MHz, CDCl$_3$) δ 7.60 (d, J=5.7 Hz, 1H), 7.4-7.3 (m, 5H), 6.37 (d, J=5.7 Hz, 1H), 5.17 (s, 2H), 2.09 (s, 3H).

b) Synthesis of 2-(2-hydroxy-2-phenylethyl)-3-[(phenylmethyl)oxy]-4H-pyran-4-one (compound P-3). To 904 g of the crude compound P-2 was added 5.88 L of THF and the solution was cooled to −60° C. 5.00 L of 1.0 M of Lithium bis(trimethylsilylamide) in THF (1.25 eq.) was added dropwise for 2 h to the solution of compound 2 at −60° C. Then, a solution of 509 g of benzaldehyde (1.2 eq.) in 800 mL of THF was added at −60° C. and the reaction mixture was aged at −60° C. for 1 h. The THF solution was poured into a mixture of 1.21 L of conc. HCl, 8.14 L of ice water and 4.52 L of EtOAc at less than 2° C. The organic layer was washed with 2.71 L of brine (twice) and the aqueous layer was extracted with 3.98 L of EtOAc. The combined organic layers were concentrated. To the mixture, 1.63 L of toluene was added and concentrated (twice) to provide toluene slurry of compound P-3. Filtration, washing with 0.90 L of cold toluene and drying afforded 955 g of compound P-3 (74% yield from compound P-1) as a solid. $^1$H NMR (300 MHz, CDCl$_3$) δ 7.62 (d, J=5.7 Hz, 1H), 7.5-7.2 (m, 10H), 6.38 (d, J=5.7 Hz, 1H), 5.16 (d, J=11.4 Hz, 1H), 5.09 (d, J=11.4 Hz, 1H), 4.95 (dd, J=4.8, 9.0 Hz, 1H), 3.01 (dd, J=9.0, 14.1 Hz, 1H), 2.84 (dd, J=4.8, 14.1 Hz, 1H).

c) Synthesis of 2-[(E)-2-phenylethenyl]-3-[(phenylmethyl)oxy]-4H-pyran-4-one (compound P-4). To a solution of 882 g of compound P-3 (1.0 eq.) in 8.82 L of THF were added 416 g of $Et_3N$ (1.5 eq.) and 408 g of methanesulfonyl chloride (1.3 eq.) at less than 30° C. After confirmation of disappearance of compound P-3, 440 mL of NMP and 1167 g of DBU (2.8 eq.) were added to the reaction mixture at less than 30° C. and the reaction mixture was aged for 30 min. The mixture was neutralized with 1.76 L of 16% sulfuric acid and the organic layer was washed with 1.76 L of 2% $Na_2SO_3$ aq. After concentration of the organic layer, 4.41 L of toluene was added and the mixture was concentrated (tree times). After addition of 4.67 L of hexane, the mixture was cooled with ice bath. Filtration, washing with 1.77 L of hexane and drying provided 780 g of compound P-4 (94% yield) as a solid. $^1H$ NMR (300 MHz, $CDCl_3$) δ 7.69 (d, J=5.7 Hz, 1H), 7.50-7.25 (m, 10H), 7.22 (d, J=16.2 Hz, 1H), 7.03 (d, J=16.2 Hz, 1H), 6.41 (d, J=5.7 Hz, 1H), 5.27 (s, 2H).

d) Synthesis of 4-oxo-3-[(phenylmethyl)oxy]-4H-pyran-2-carboxylic acid (compound P-5). To a mixture of 822 g of compound P-4 (1.0 eq.) and 11.2 g of $RuCl_3.nH_2O$ (0.02 eq.) in 2.47 L of MeCN, 2.47 L of EtOAc and 2.47 L of $H_2O$ was added 2310 g of $NaIO_4$ (4.0 eq.) at less than 25° C. After aging for 1 h, 733 g of $NaClO_2$ (3.0 eq.) was added to the mixture at less than 25° C. After aging for 1 h, precipitate was filtered and washed with 8.22 L of EtOAc. To the filtrate, 1.64 L of 50% $Na_2S_2O_3$ aq, 822 mL of $H_2O$ and 630 mL of coc.HCl were added. The aqueous layer was extracted with 4.11 L of EtOAc and the organic layers were combined and concentrated. To the residue, 4 L of toluene was added and the mixture was concentrated and cooled with ice bath. Filtration, washing with 1 L of toluene and drying provided 372 g of compound P-5 (56% yield) as a solid. $^1H$ NMR (300 MHz, $CDCl_3$) δ 7.78 (d, J=5.7 Hz, 1H), 7.54-7.46 (m, 2H), 7.40-7.26 (m, 3H), 6.48 (d, J=5.7 Hz, 1H), 5.6 (brs, 1H), 5.31 (s, 2H).

e) Synthesis of 1-(2,3-dihydroxypropyl)-4-oxo-3-[(phenylmethyl)oxy]-1,4-dihydro-2-pyridinecarboxylic acid (compound P-6). A mixture of 509 g of compound P-5 (1.0 eq.) and 407 g of 3-amino-propane-1,2-diol (2.5 eq.) in 1.53 L of EtOH was stirred at 65° C. for 1 h and at 80° C. for 6 h. After addition of 18.8 g of 3-Amino-propane-1,2-diol (0.1 eq.) in 200 mL of EtOH, the mixture was stirred at 80° C. for 1 h. After addition of 18.8 g of 3-amino-propane-1,2-diol (0.1 eq.) in 200 mL of EtOH, the mixture was stirred at 80° C. for 30 min. After cooling and addition of 509 mL of $H_2O$, the mixture was concentrated. To the residue, 2.54 L of $H_2O$ and 2.54 L of AcOEt were added. After separation, the aqueous layer was washed with 1.02 L of EtOAc. To the aqueous layer, 2.03 L of 12% sulfuric acid was added at less than 12° C. to give crystal of compound P-6. Filtration, washing with 1.53 L of cold $H_2O$ and drying provided 576 g of compound P-6 (83% yield) as a solid. $^1H$ NMR (300 MHz, DMSO-$d_6$) δ 7.67 (d, J=7.5 Hz, 1H), 7.5-7.2 (m, 5H), 6.40 (d, J=7.5 Hz, 1H), 5.07 (s, 2H), 4.2-4.0 (m, 1H), 3.9-3.6 (m, 2H), 3.38 (dd, J=4.2, 10.8 Hz, 1H), 3.27 (dd, J=6.0, 10.8 Hz, 1H).

f) Synthesis of methyl 1-(2,3-dihydroxypropyl)-4-oxo-3-[(phenylmethyl)oxy]-1,4-dihydro-2-pyridinecarboxylate (compound P-7). To a slurry of 576 g of compound P-6 (1.0 eq.: 5.8% of $H_2O$ was contained) in 2.88 L of NMP were added 431 g of $NaHCO_3$ (3.0 eq.) and 160 mL of methyl iodide (1.5 eq.) and the mixture was stirred at room temperature for 4 h. After cooling to 5° C., 1.71 L of 2N HCl and 1.15 L of 20% NaClaq were added to the mixture at less than 10° C. to give crystal of compound 7. Filtration, washing with 1.73 L of $H_2O$ and drying provided 507 g of compound P-7 (89% yield) as a solid. $^1H$ NMR (300 MHz, DMSO-$d_6$) δ 7.59 (d, J=7.5 Hz, 1H), 7.40-7.28 (m, 5H), 6.28 (d, J=7.5 Hz, 1H), 5.21 (d, J=5.4 Hz, 1H), 5.12 (d, J=10.8 Hz, 1H), 5.07 (d, J=10.8 Hz, 1H), 4.83 (t, J=5.7 Hz, 1H), 3.97 (dd, J=2.4, 14.1 Hz, 1H), 3.79 (s, 3H), 3.70 (dd, J=9.0, 14.4 Hz, 1H), 3.65-3.50 (m, 1H), 3.40-3.28 (m, 1H), 3.26-3.14 (m, 1H).

g) Synthesis of methyl 1-(2,2-dihydroxyethyl)-4-oxo-3-[(phenylmethyl)oxy]-1,4-dihydro-2-pyridinecarboxylate (compound P-8). To a mixture of 507 g of compound P-7 (1.0 eq.) in 5.07 L of MeCN, 5.07 L of $H_2O$ and 9.13 g of AcOH (0.1 eq.) was added 390 g of $NaIO_4$ (1.2 eq.) and the mixture was stirred at room temperature for 2 h. After addition of 1.52 L of 10% $Na_2S_2O_3$ aq., the mixture was concentrated and cooled to 10° C. Filtration, washing with $H_2O$ and drying provided 386 g of compound P-8 (80% yield) as a solid. $^1H$ NMR (300 MHz, DMSO-$d_6$) δ 7.62 (d, J=7.5 Hz, 1H), 7.42-7.30 (m, 5H), 6.33 (d, J=6.0 Hz, 2H), 6.29 (d, J=7.5 Hz, 1H), 5.08 (s, 2H), 4.95-4.85 (m, 1H), 3.80 (s, 3H), 3.74 (d, J=5.1 Hz, 2H).

h) Synthesis of (4R,12aS)-4-methyl-7-[(phenylmethyl)oxy]-3,4,12,12a-tetrahydro-2H-pyrido[1',2':4,5]pyrazino[2,1-b][1,3]oxazine-6,8-dione (compound P-9). After dissolution of a mixture of 378 g of compound P-8 (1.0 eq.) in 3.78 L of MeOH by heating, the solution was concentrated. To the residue, 1.51 L of toluene was added and the mixture was concentrated. To the residue, 1.89 L of toluene, 378 mL of AcOH and 137 g of (R)-3-Amino-butan-1-ol (1.3 eq.) were added and the mixture was heated to 90° C., stirred at 90° C. for 2.5 h and concentrated. To the residue, 1.89 L of toluene was added and the mixture was concentrated. The residue was extracted with 3.78 L and 1.89 L of $CHCl_3$ and washed with 2×1.89 L of $H_2O$. The organic layers were combined and concentrated. To the residue, 1.89 L of EtOAc was added and the mixture was concentrated. After addition of 1.89 L of EtOAc, filtration, washing with 1.13 L of EtOAc and drying provided 335 g of compound P-9 (83% yield) as a solid. $^1H$ NMR (300 MHz, $CDCl_3$) δ 7.70-7.58 (m, 2H), 7.40-7.24 (m, 3H), 7.14 (d, J=7.5 Hz, 2H), 6.47 (d, J=7.5 Hz, 1H), 5.35 (d, J=10.2 Hz, 1H), 5.28 (d, J=10.2 Hz, 1H), 5.12 (dd, J=3.9, 6.3 Hz, 1H), 5.05-4.90 (m, 1H), 4.07 (dd, J=3.9, 13.5 Hz, 1H), 4.00-3.86 (m, 3H), 2.23-2.06 (m, 1H), 1.48 (ddd, J=2.4, 4.5, 13.8 Hz, 1H), 1.30 (d, J=6.9 Hz, 3H).

i) Synthesis of (4R,12aS)-9-bromo-4-methyl-7-[(phenylmethyl)oxy]-3,4,12,12a-tetrahydro-2H-pyrido[1',2':4,5]pyrazino[2,1-b][1,3]oxazine-6,8-dione (compound P-10). To a slurry of 332 g of compound P-9 (1.0 eq.) in 1.66 L of NMP was added 191 g of NBS (1.1 eq.) and the mixture was stirred at room temperature for 2 h. After addition of 1.26 L of $H_2O$, the mixture was stirred for 30 min. After addition of 5.38 L of $H_2O$ and aging of the mixture at 10° C. for 30 min and at 5° C. for 1 h, filtration, washing with 1.33 L of cold $H_2O$ and drying provided 362 g of compound P-10 (89% yield) as a solid. $^1H$ NMR (300 MHz, $CDCl_3$) δ 7.69-7.63 (m, 2H), 7.59 (s, 1H), 7.38-7.24 (m, 3H), 5.33 (d, J=10.2 Hz, 1H), 5.25 (d, J=9.9 Hz, 1H), 5.12 (dd, J=3.9, 5.7 Hz, 1H), 5.05-4.90 (m, 1H), 4.11 (dd, J=3.9, 13.2 Hz, 1H), 4.02-3.88

(m, 3H), 2.21-2.06 (m, 1H), 1.49 (ddd, J=2.4, 4.5, 14.1 Hz, 1H), 1.31 (d, J=6.9 Hz, 3H).

j) Synthesis of (4R,12aS)-N-[(2,4-difluorophenyl)methyl]-4-methyl-6,8-dioxo-7-[(phenylmethyl)oxy]-3,4,6,8,12,12a-hexahydro-2H-pyrido[1',2':4,5]pyrazino[2,1-b][1,3]oxazine-9-carboxamide (compound P-11). Under carbon mono-oxide atmosphere, a mixture of 33.5 g of compound P-10 (1.0 eq.), 34.8 mL of i-Pr$_2$NEt (2.5 eq.), 14.3 mL of 2,4-difluorobenzylamine (1.5 eq.) and 4.62 g of Pd(PPh$_3$)$_4$ (0.05 eq.) in 335 mL of DMSO was stirred at 90° C. for 5.5 h. After cooling, precipitate was filtered and washed with 50 mL of 2-propanol. After addition of 502 mL of H$_2$O and 670 mL of AcOEt to the filtrate, the organic layer was washed with 335 mL of 0.5N HClaq. and 335 mL of H$_2$O and the aqueous layer was extracted with 335 mL of AcOEt. The organic layers were combined and concentrated. To the residue, 150 mL of 2-propanol was added and the mixture was concentrated. After addition of 150 mL of 2-propanol, concentration, cooling to 20° C. and filtration, crude crystal of compound P-11 was obtained. After dissolution of the crude crystal in 380 mL of acetone by heating, precipitate was filtered and the filtrate was concentrated. After addition of 200 mL of EtOH, concentration, addition of 150 mL of EtOH, concentration, cooling and filtration, crude crystal of compound P-11 was obtained. After dissolution of the crude crystal in 450 mL of acetone by heating, the solution was concentrated. To the residue, 150 mL of 2-propanol was added and the mixture was concentrated (twice). After cooling of the residue, filtration, washing with 2-propanol and drying provided 34.3 g of compound P-11 (84% yield) as a solid. $^1$H NMR (300 MHz, CDCl$_3$) δ 10.40 (t, J=6.0 Hz, 1H), 8.35 (s, 1H), 7.66-7.58 (m, 2H), 7.42-7.24 (m, 5H), 6.78-6.74 (m, 2H), 5.30 (d, J=9.9 Hz, 1H), 5.26 (d, J=10.2 Hz, 1H), 5.15 (dd, J=3.9, 5.7 Hz, 1H), 5.05-4.90 (m, 1H), 4.64 (d, J=5.4 Hz, 2H), 4.22 (dd, J=3.9, 13.5, 1H), 4.09 (dd, J=6.0, 13.2 Hz, 1H), 4.02-3.88 (m, 2H), 2.24-1.86 (m, 1H), 1.50 (ddd, J=2.4, 4.5, 14.1 Hz, 1H), 1.33 (d, J=7.2 Hz, 3H).

k) Synthesis of (4R,12aS)-N-[(2,4-difluorophenyl)methyl]-7-hydroxy-4-methyl-6,8-dioxo-3,4,6,8,12,12a-hexahydro-2H-pyrido[1',2':4,5]pyrazino[2,1-b][1,3]oxazine-9-carboxamide (compound 1a) Under hydrogen atmosphere, a mixture of 28.0 g of compound P-11 (1.0 eq.) and 5.6 g of 10% Pd—C in 252 mL of THF and 28 mL of MeOH was stirred for 1 h. After precipitate (Pd—C) was filtered and washed with 45 mL of THF, 5.6 g of 10% Pd—C was added and the mixture was stirred for 1.5 h under hydrogen atmosphere. After Pd—C was filtered and washed with 150 mL of CHCl$_3$/MeOH (9/1), the filtrate was concentrated. After dissolution of the residue in 1.38 L of EtOH by heating, the solution was gradually cooled to room temperature. After filtration, the filtrate was concentrated and cooled. Filtration, washing with EtOH and drying provided 21.2 g of compound 1a (92% yield) as a solid. $^1$H NMR (300 MHz, DMSO-d$_6$) δ 12.51 (s, 1H), 10.36 (t, J=5.7 Hz, 1H), 8.50 (s, 1H), 7.39 (td, J=8.7, 6.3 Hz, 1H), 7.24 (ddd, J=2.6, 9.5, 10.8 Hz, 1H), 7.12-7.00 (m, 1H), 5.44 (dd, J=3.9, 5.7 Hz, 1H), 4.90-4.70 (m, 1H), 4.65-4.50 (m, 1H), 4.54 (d, J=5.1 Hz, 2H), 4.35 (dd, J=6.0, 13.8 Hz, 1H), 4.10-3.98 (m, 1H), 3.96-3.86 (m, 1H), 2.10-1.94 (m, 1H), 1.60-1.48 (m, 1H), 1.33 (d, J=6.9 Hz, 3H).

l). Synthesis of (4R,12aS)-N-[(2,4-difluorophenyl)methyl]-7-hydroxy-4-methyl-6,8-dioxo-3,4,6,8,12,12a-hexahydro-2H-pyrido[1',2':4,5]pyrazino[2,1-b][1,3]oxazine-9-carboxamide sodium salt (compound 1b). After dissolution of 18.0 g of compound 1a (1.0 eq.) in 54 mL of EtOH by heating, followed by filtration, 21.5 mL of 2N NaOHaq. (1.0 eq.) was added to the solution at 80° C. The solution was gradually cooled to room temperature. Filtration, washing with 80 mL of EtOH and drying provided 18.8 g of compound 1b (99% yield) as a solid. $^1$H NMR (300 MHz, DMSO-d$_6$) δ 10.70 (t, J=6.0 Hz, 1H), 7.89 (s, 1H), 7.40-7.30 (m, 1H), 7.25-7.16 (m, 1H), 7.06-6.98 (m, 1H), 5.22-5.12 (m, 1H), 4.87-4.74 (m, 1H), 4.51 (d, J=5.4 Hz, 2H), 4.35-4.25 (m, 1H), 4.16 (dd, J=1.8, 14.1 Hz, 1H), 4.05-3.90 (m, 1H), 3.86-3.74 (m, 1H), 2.00-1.72 (m, 1H), 1.44-1.32 (m, 1H), 1.24 (d, J=6.9 Hz, 3H).

Example 1

{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl methyl carbonate

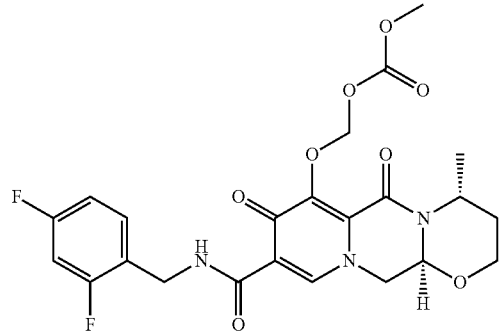

a) Chloromethyl methyl carbonate. Chloromethyl chloridocarbonate (3 ml, 33.7 mmol) was dissolved in dichloromethane (10 mL) and cooled to 0° C. Methanol (1.36 mL, 33.7 mmol) was added dropwise, followed by pyridine (2.73 mL, 33.7 mmol) dropwise. The white suspension was stirred at 0° C. and allowed to warm to ambient temperature and stirred for 14 hours. The suspension was quenched with water, diluted with aqueous citric acid, extracted with dichloromethane, washed with sodium bicarbonate, brine, dried over sodium sulfate and concentrated under reduced pressure to give chloromethyl methyl carbonate as a clear colorless oil. $^1$H NMR (CDCl$_3$) δ 5.72 (s, 2H), 3.96 (s, 3H).

b) Iodomethyl methyl carbonate. Chloromethyl methyl carbonate (2.05 g, 16.46 mmol) was dissolved in acetone and sodium iodide (3.70 g, 24.69 mmol) was added and the reaction was heated at 40° C. for 15 hours. The yellow suspension was allowed to cool to ambient temperature, concentrated under reduced pressure, diluted with water and aqueous sodium thiosulfate, extracted with dichloromethane, washed with brine, dried over sodium sulfate, and concentrated under reduced pressure to give iodomethyl methyl carbonate as a clear yellow oil. $^1$H NMR (CDCl$_3$) δ 5.92 (s, 2H), 3.93 (s, 3H).

c) {[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl methyl carbonate. (4R,12aS)-N-[(2,4-Difluorophenyl)methyl]-7-hydroxy-4-methyl-6, 8-dioxo-3,4,6,8,12,12a-hexahydro-2H-pyrido[1',2':4,5] pyrazino[2,1-b][1,3]oxazine-9-carboxamide sodium salt (100 mg, 0.227 mmol) and potassium carbonate (94 mg, 0.680 mmol) were suspended in water and tetrabutylammonium hydrogen sulfate (77 mg, 0.227 mmol) was added followed by dichloromethane. Stirring 5 min gave a clear biphasic solution. Iodomethyl methyl carbonate (196 mg, 0.906 mmol) was added as a solution in dichloromethane. Stirring 3 hours gave complete reaction. The reaction was diluted with water, dichloromethane, extracted with dichloromethane, washed with sodium bicarbonate, brine, dried over sodium sulfate, and purified by silica-gel chromatography (1-12% methanol/dichloromethane gradient elution). The isolate was re-dissolved in ethyl acetate and washed 4 times with water, and twice with brine, and dried over sodium sulfate. Concentration under reduced pressure yielded the title compound as a white solid. $^1$H NMR (CDCl$_3$) δ 10.24 (m, 1H), 8.38 (s, 1H), 7.28 (m, 1H), 6.77 (m, 2H), 5.79 (m, 2H), 5.16 (m, 1H), 4.97 (m, 1H), 4.56 (d, J=6 Hz, 2H), 4.25 (dd, J=13.2, 3.6 Hz, 1H), 4.13 (m, 1H), 3.92 (m, 2H), 3.76 (s, 3H), 2.13 (m, 1H), 1.46 (m, 1H), 1.29 (d, J=7.2 Hz, 3H). ES$^+$MS: 508 (M+1).

Example 2

{[(4R,12aS)-9-({[(2,4-Difluorophenyl)methyl] amino}carbonyl)-4-methyl-6,8-dioxo-3,4,6,8,12,12a-hexahydro-2H-pyrido[1',2':4,5]pyrazino[2,1-b][1,3] oxazin-7-yl]oxy}methyl 2-(methyloxy)ethyl carbonate

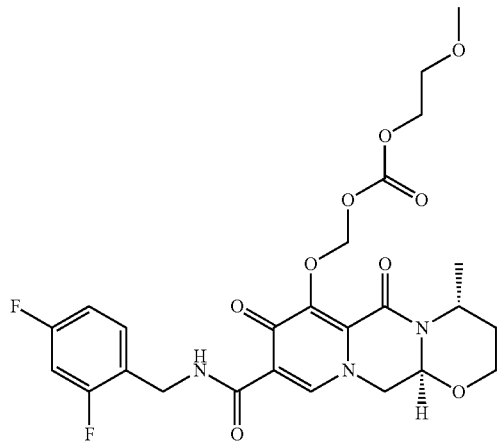

The title compound was prepared from iodomethyl 2-(methyloxy)ethyl carbonate (59 mg, 0.227 mmol) (prepared in a similar manner to example 1), (4R,12aS)-N-[(2,4-Difluorophenyl)methyl]-7-hydroxy-4-methyl-6,8-dioxo-3,4,6,8, 12,12a-hexahydro-2H-pyrido[1',2':4,5]pyrazino[2,1-b][1,3] oxazine-9-carboxamide sodium salt (50 mg, 0.113 mmol), potassium carbonate (47 mg, 0.340 mmol), and tetrabutylammonium hydrogen sulfate (39 mg, 0.113 mmol), using a similar process to that described in example 1. $^1$H NMR (CDCl$_3$) δ 10.32 (m, 1H), 8.37 (s, 1H), 7.31 (m, 1H), 6.77 (m, 2H), 5.83 (m, 2H), 5.16 (m, 1H), 4.92 (m, 1H), 4.57 (d, J=6 Hz, 2H), 4.29-4.23 (m, 3H), 4.16 (m, 1H), 3.93 (m, 2H), 3.62-3.57 (m, 2H), 3.32 (s, 3H), 2.13 (m, 1H), 1.46 (m, 1H), 1.30 (d, J=7.2 Hz, 3 H). ES$^+$MS: 552 (M+1).

Example 3

{[(4R,12aS)-9-({[(2,4-Difluorophenyl)methyl] amino}carbonyl)-4-methyl-6,8-dioxo-3,4,6,8,12,12a-hexahydro-2H-pyrido[1',2':4,5]pyrazino[2,1-b][1,3] oxazin-7-yl]oxy}methyl 2-hydroxyethyl carbonate

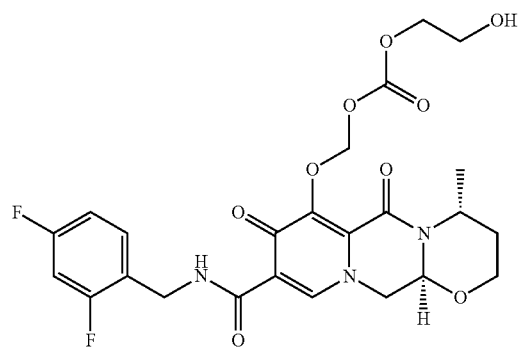

a) {[(4R,12aS)-9-({[(2,4-Difluorophenyl)methyl] amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-[(phenylmethyl)oxy]ethyl carbonate. The title compound was prepared from iodomethyl 2-[(phenylmethyl)oxy]ethyl carbonate (314 mg, 0.933 mmol) (prepared in a similar manner to example 1), (4R,12aS)-N-[(2,4-Difluorophenyl)methyl]-7-hydroxy-4-methyl-6,8-dioxo-3,4,6,8,12,12a-hexahydro-2H-pyrido[1',2':4,5]pyrazino[2,1-b][1,3]oxazine-9-carboxamide sodium salt (103 mg, 0.233 mmol), potassium carbonate (97 mg, 0.700 mmol), and tetrabutylammonium hydrogen sulfate (79 mg, 0.233 mmol), using a similar process to that described in example 1. $^1$H NMR (CDCl$_3$) δ 10.23 (m, 1 H), 8.36 (s, 1H), 7.33-7.23 (m, 6H), 6.78 (m, 2H), 5.84 (m, 2H), 5.13 (m, 1H), 4.88 (m, 1H), 4.57-4.51 (m, 4H), 4.30 (m, 2H), 4.21 (m, 1H), 4.10 (m, 1H), 3.88 (m, 2H), 3.72-3.66 (m, 2H), 2.08 (m, 1H), 1.40 (m, 1H), 1.25 (d, J=6.8 Hz, 3H). ES$^+$MS: 628 (M+1).

b) {[(4R,12aS)-9-({[(2,4-Difluorophenyl)methyl] amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-hydroxyethyl carbonate. The product prepared as described in step (a) above (125 mg, 0.199 mmol) was dissolved in methanol/ethyl acetate mixture and 10 w.t. % palladium on carbon (85 mg) was added under a nitrogen atmosphere. The reaction was stirred at 1 atm hydrogen and then at 60 psi hydrogen for 14 hours. Acetic acid (1 mL) was added and the reaction was stirred at 45 psi for 8 hours. The mixture was filtered through celite and concentrated under reduced pressure. Purification by silica gel chromatography yielded the title compound as a white solid. $^1$H NMR (CDCl$_3$) δ 10.12 (m, 1H), 8.35 (s, 1H), 7.32 (m, 1H), 6.78 (m, 2H), 5.92 (d, J=6.8 Hz, 1H), 5.85 (d, J=6.8 Hz, 1H), 5.17 (m, 1H), 4.88 (m, 1H), 4.58 (m, 2H), 4.38-4.29 (m, 2H), 4.23

(m, 1H), 4.11 (m, 1H), 3.93-3.82 (m, 4H), 3.29 (m, 1H), 2.14 (m, 1H), 1.49 (m, 1H), 1.33 (d, J=7.2 Hz, 3H). ES⁺MS: 538 (M+1).

Example 4

{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(phosphonooxy)ethyl carbonate

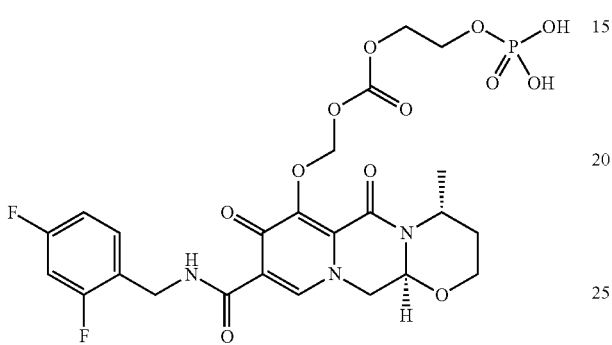

a) 2-({Bis[(phenylmethyl)oxy]phosphoryl}oxy)ethyl {[(4R,12aS)-9-({[(2,4-difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl carbonate. Dibenzyl N,N-diisopropyl-phosphoramidite was added to a mixture of {[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-hydroxyethyl carbonate (example 3) (43 mg, 0.080 mmol) and tetrazole (67 mg, 0.960 mmol) in dichloromethane at ambient temperature and stirred 14 hours. The reaction was cooled in an ice-water bath, and m-CPBA (110 mg, 0.640 mmol) was added carefully and the mixture was stirred for 30 minutes letting the ice-bath expire. Sodium thiosulfate solution was added, and the mixture was extracted with dichloromethane, washed with sodium bicarbonate solution and brine, and dried over sodium sulfate. Purification by silica gel chromatography afforded the title compound as a white solid. ¹H NMR (CDCl₃) δ 10.22 (m, 1H), 8.33 (s, 1H), 7.32-7.26 (m, 11H), 6.78 (m, 2H), 5.83 (m, 2H), 5.10 (m, 1H), 5.02-4.98 (m, 4H), 4.87 (m, 1H), 4.57 (m, 2H), 4.29 (m, 2H), 4.21-4.13 (m, 3H), 4.00 (m, 1H), 3.90-3.86 (m, 2H), 2.07 (m, 1H), 1.39 (m, 1H), 1.25 (d, J=7.2 Hz, 3H). ES⁺ MS: 798 (M+1).

b) {[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(phosphonooxy)ethyl carbonate. Product prepared as described in step (a) above (52 mg, 0.065 mmol) was dissolved in methanol and 10 w.t. % palladium on carbon (25 mg) was added and the reaction was stirred under 1 atm hydrogen for 30 minutes. The mixture was filtered through celite and concentrated under reduced pressure to afford the title compound as a white solid. ¹H NMR (methanol-d₄, CDCl₃) δ 10.19 (br s, 1H), 8.28 (br s, 1H), 7.32 (m, 1H), 6.70 (m, 2H), 5.64 (br s, 2H), 5.13 (br s, 1H), 4.81 (br s, 1H), 4.48-3.40 (m, 10H), 2.03 (m, 1H), 1.40 (m, 1H), 1.21 (m, 3H). ES⁻MS: 616 (M−1).

Example 5

{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(4-morpholinyl)ethyl carbonate hydrochloric acid salt

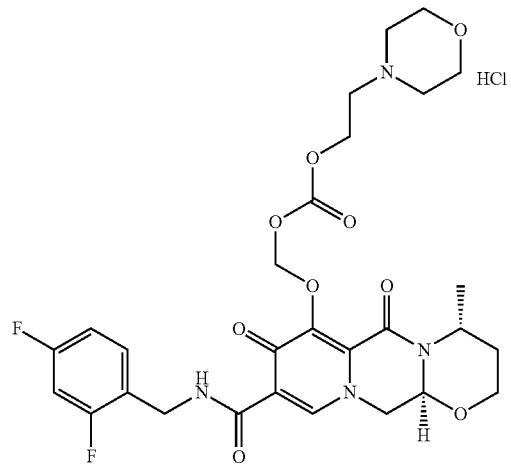

a) Chloromethyl 4-nitrophenyl carbonate. N-methyl morpholine (1.24 mL, 11.24 mmol) was added dropwise to a solution of 4-nitrophenol (1.56 g, 11.24 mmol) in dichlormethane at 0° C., followed by dropwise addition of chloromethyl chloridocarbonate (1 mL, 11.24 mmol) and the mixture was stirred for 14 hours at ambient temperature. The reaction was diluted with citric acid solution, extracted with dichloromethane, washed with aqueous sodium bicarbonate, brine, and dried over sodium sulfate to yield the title compound as a yellow oil. ¹H NMR (CDCl₃) δ 8.29 (m, 2H), 7.40 (m, 2H), 5.82 (s, 2H).

b) Iodomethyl 4-nitrophenyl carbonate. Chloromethyl 4-nitrophenyl carbonate (2.47 g, 10.67 mmol), sodium iodide (1.76 g, 11.73 mmol) were suspended in acetone and heated overnight at 45° C. The yellow suspension was allowed to cool to ambient temperature, concentrated under reduced pressure, diluted with water and aqueous sodium thiosulfate, extracted with dichloromethane, washed with brine, dried over sodium sulfate, and concentrated under reduced pressure to give the title compound as a clear yellow oil. ¹H NMR (CDCl₃) δ 8.30 (dd, J=7.2, 2.4 Hz, 2H), 7.42 (dd, J=6.8, 2 Hz, 2H), 6.06 (s, 2H).

c) {[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 4-nitrophenyl carbonate. The title compound was prepared from (4R,12aS)-N-[(2,4-Difluorophenyl)methyl]-7-hydroxy-4-methyl-6,8-dioxo-3,4,6,8,12,12a-hexahydro-2H-pyrido[1',2':4,5]pyrazino[2,1-b][1,3]oxazine-9-carboxamide sodium salt (1.8 g, 4.29 mmol), iodomethyl 4-nitrophenyl carbonate (2.77 g, 8.58 mmol), potassium carbonate (1.78 g, 12.88 mmol), and tetrabutylammonium hydrogen sulfate (1.46 g, 4.29 mmol) in a manner similar to that described in example 1, step c. $^1$H NMR (CDCl$_3$) δ 10.17 (m, 1H), 8.37 (s, 1H), 7.40 (m, 2H), 7.30 (m, 1H), 6.78 (m, 2H), 5.97 (d, J=6.4 Hz, 1H), 5.92 (d, J=6.4 Hz, 1H), 5.19 (m, 2H), 4.89 (m, 2H), 4.59 (m, 2H), 4.22 (m, 1H), 4.13 (m, 1H), 3.93 (m, 1H), 2.12 (m, 1 HO, 1.40 (m, 1H), 1.29 (m, 3H). ES$^+$MS: 615 (M+1).

d) {[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(4-morpholinyl)ethyl carbonate hydrochloric acid salt. A mixture of intermediate prepared as described in step b (425 mg, 0692 mmol), 2-(4-morpholinyl)ethanol (excess), triethylamine (0.29 mL, 2.08 mmol) and DMAP (84 mg, 0.692 mmol) in acetonitrile was stirred at reflux for several hours. The reaction was cooled and concentrated under reduced pressure, diluted with water and dichloromethane, and extracted. The combined organics were washed with aqueous sodium bicarbonate, brine, and dried over sodium sulfate. Purification by reverse-phase hplc afforded the title compound as the trifluoroacetic acid salt. Re-dissolved isolate in dichloromethane and washed organic layer with sodium bicarbonate solution. Dried over sodium sulfate and concentrated under reduced. The intermediate prepared as described above (124 mg, 0.204 mmol) was dissolved in dioxane and placed in an ice-water bath. Hydrochloric acid (0.2 mL, 1N solution) was added and the reaction was stirred 15 minutes at ambient temperature. The mixture was concentrated under reduced pressure to yield the title compound as a white solid. $^1$H NMR (methanol-d$_4$/CDCl$_3$) δ 13.60 (m, 1H), 10.11 (m, 1H), 8.36 (s, 1H), 7.32 (m, 1H), 6.79 (m, 2H), 5.84 (m, 2H), 5.18 (m, 1H), 4.91 (m, 1H), 4.74 (m, 1H), 4.60 (m, 2H), 4.35-4.10 (m, 4H), 3.97-3.93 (m, 3H), 3.51 (m, 2H), 3.36 (m, 2H), 3.04 (m, 2H), 2.14 (m, 1H), 1.49 (m, 1H), 1.35 (m, 3H). ES$^+$MS: 607 (M+1).

Example 6

Rat Pharmacokinetics

Fasted male CD rats received the compound of Example 2 as an oral suspension dose (5 mg parent equivalent/kg in 0.1% hydroxypropylmethylcellulose/0.1% Tween-80) administered via an oral gavage needle. Blood samples (0.2 mL each) were drawn from a surgically implanted femoral vein cannula at timed intervals for 24 h following dose administration; all samples were drawn using EDTA-treated syringes. Each blood sample was combined with 0.02 mL of a protease inhibitor solution [e-amino-n-caproic acid, benzamide HCl, and 4-(2-aminoethyl)benzenesulfonyl fluoride HCl in water] to inhibit ex vivo conversion of prodrug to parent, vortexed to mix, and centrifuged (4000×g, 4° C., 20 min) to harvest plasma. Prodrug and parent concentrations in plasma samples were quantitated by LC/MS/MS analysis. Area under the plasma concentration-time curve was estimated using non-compartmental analysis methods (WinNonlin Professional 4.1)

The invention claimed is:
1. A compound of formula (I):

wherein:
R$^1$ is C$_1$-C$_8$alkyl or LR$^2$;
L is alkylene;
R$^2$ is
a) hydroxy;
b) alkoxy;
c) OR$^3$ wherein R$^3$ is P(O)(OH)$_2$ or alkoxy;
d) heterocyclyl optionally substituted with oxo or C$_1$-C$_8$alkyl;
e) C(O)OR$^4$ wherein R$^4$ is H, C$_1$-C$_8$alkyl, or XR$^5$ wherein X is alkylene and R$^5$ is C$_6$-C$_{10}$aryl, heterocyclyl, or NR$^6$R$^7$ wherein R$^6$ and R$^7$ are independently selected from the group consisting of H and C$_1$-C$_8$alkyl;
f) NR$^6$R7$^7$;
g) C(O)NR$^8$R$^9$ wherein R$^8$ and R$^9$ are independently selected from the group consisting of H and XR$^5$; or
h) C(O)R$^{10}$ wherein R$^{10}$ is heterocyclyl optionally substituted with XR$^{11}$ wherein R$^{11}$ is heterocyclyl;
or a pharmaceutically acceptable salt thereof.
2. A compound of formula (I) according to claim 1 wherein R$^1$ is C$_{1-8}$alkyl.
3. A compound of formula (I) according to claim 1 wherein R$^1$ is LR$^2$ wherein L is C$_{1-8}$alkylene and R$^2$ is hydroxy or alkoxy.
4. A compound of formula (I) according to claim 1 wherein R$^1$ is LR$^2$ wherein L is C$_{1-8}$alkylene and R$^2$ and —OP(O)(OH)$_2$ or a pharmaceutically acceptable salt thereof.
5. A compound of formula (I) according to claim 1 wherein R$^1$ is LR$^2$ wherein L is C$_{1-8}$alkylene and R$^2$ and heterocyclyl or a pharmaceutically acceptable salt thereof.
6. A compound selected from the group consisting of:
{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl methyl carbonate;
{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(methyloxy)ethyl carbonate;
{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-hydroxyethyl carbonate;
{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(phosphonooxy)ethyl carbonate;

{[(4R,12aS)-9-({[(2,4-Difluorophenyl)methyl]amino}carbonyl)-4-methyl-6,8-dioxo-3,4,6,8,12,12a-hexahydro-2H-pyrido[1',2':4,5]pyrazino[2,1-b][1,3]oxazin-7-yl]oxy}methyl 2-(4-morpholinyl)ethyl carbonate; and pharmaceutically acceptable salts thereof.

7. A compound according to any one of claims 1 to 6 wherein the pharmaceutically acceptable salt is a hydrochloride salt.

8. A pharmaceutical composition comprising an effective amount of a compound according to any one of claims 1 to 6 together with a pharmaceutically acceptable carrier.

9. A pharmaceutical composition according to claim 8 in the form of a tablet, capsule, liquid or suspension.

10. A pharmaceutical composition according to claim 8 wherein the pharmaceutically acceptable salt is a hydrochloride salt.

* * * * *